United States Patent
Ron et al.

(10) Patent No.: US 12,274,881 B2
(45) Date of Patent: Apr. 15, 2025

(54) METHOD AND PROCESS FOR PLACEMENT AND FIXATION OF A SURGICAL IMPLANT

(71) Applicant: Nyxoah SA, Mont Saint Guibert (BE)

(72) Inventors: Udi Ron, Tel Aviv-Jaffa (IL); Pierre Gianello, Rixensart (BE); Richard Lewis, Perth (AU); Chloe Bertolus, Paris (FR)

(73) Assignee: Nyxoah SA, Mont Saint Guibert (BE)

( * ) Notice: Subject to any disclaimer, the term of this patent is extended or adjusted under 35 U.S.C. 154(b) by 300 days.

(21) Appl. No.: 17/636,227

(22) PCT Filed: Aug. 26, 2020

(86) PCT No.: PCT/EP2020/073878
§ 371 (c)(1),
(2) Date: Feb. 17, 2022

(87) PCT Pub. No.: WO2021/037927
PCT Pub. Date: Mar. 4, 2021

(65) Prior Publication Data
US 2022/0339439 A1    Oct. 27, 2022

(30) Foreign Application Priority Data
Aug. 26, 2019 (IL) .......................... 268936

(51) Int. Cl.
*A61N 1/36* (2006.01)
(52) U.S. Cl.
CPC .................... *A61N 1/3611* (2013.01)
(58) Field of Classification Search
CPC .............. A61N 1/3611; A61N 1/0548; A61N 1/36114; A61N 1/36003; A61N 1/0551; A61N 1/3601
See application file for complete search history.

(56) References Cited

U.S. PATENT DOCUMENTS

| 6,117,072 A | 9/2000 | Fowler, Jr. |
| 8,577,466 B2 | 11/2013 | Mashiach |

(Continued)

FOREIGN PATENT DOCUMENTS

| JP | H06-054861 A | 1/1994 |
| JP | H09-238950 A | 9/1997 |

(Continued)

OTHER PUBLICATIONS

International Search Report and Written Opinion in PCT Application No. PCT/EP2020/073878 dated Feb. 2, 2021 (11 pages).

(Continued)

*Primary Examiner* — Paula J Stice
(74) *Attorney, Agent, or Firm* — Finnegan, Henderson, Farabow, Garrett & Dunner LLP (57) ABSTRACT

A method of treating obstructive sleep apnea according to this disclosure may include: providing an implant comprising a substantially planar central body portion having a top side and a bottom side; at least two adjustable wing portions; and at least two connecting members, each one of the at least two connecting members extending from opposite sides of the central body portion, the each one of the at least two connecting members being configured for flexibly connecting each one of the at least two wing portions at opposite sides to said central body portion; forming a surgical opening to expose a genioglossus muscle; exposing a branch of a hypoglossal nerve for stimulation by the implant at least on one side of the geniouglossus; forming at least one pocket on at least one side of the geniouglossus; such that the pocket dimensions are configured to fit the at least one of the at least two wing portions of the device; inserting an implant device through the surgical opening such that the central body extends over the geniouglossus and each one of the wing (Continued)

portions is received in the respective at least one pocket; and securing the implant device to the muscle.

8 Claims, 7 Drawing Sheets

(56) References Cited

U.S. PATENT DOCUMENTS

| | | | |
|---|---|---|---|
| 9,415,216 B2 | 8/2016 | Mashiach | |
| 2013/0072999 A1* | 3/2013 | Mashiach | A61N 1/0504 607/42 |
| 2014/0371802 A1 | 12/2014 | Mashiach et al. | |

FOREIGN PATENT DOCUMENTS

| | | |
|---|---|---|
| WO | WO 2013/046048 A2 | 4/2013 |
| WO | WO 2018/158305 A1 | 9/2018 |

OTHER PUBLICATIONS

Neelapu BC, Kharband OP, Sardana HK et al, Craniofacial and upper airway morphology in adult obstructive sleep apnea patients: A systematic review and meta-analysis of cephalometric studies. Sleep Med Rev. Feb. 2017; 31:79-90. doi:10.1016/j.smrv.2016.01. 007. Epub Jan. 30, 2016.

Eckert DJ, White DP, Jordan AS, Malhotra A, Wellman A Am J Respir Crit Care Med. Oct. 15, 2013; 188(8):996-1004. doi: 10.1164/rccm.201303-0448OC.

Schwartz AR1, Bennett ML, Smith PL, De Backer W, Hedner J, Boudewyns A, Van de Heyning P, Ejnell H, Hochban W, Knaac L, Podszus T, Penzel T, Peter JH, Goding GS, Erickson DJ, Testerman R, Ottenhoff F, Eisele DW. Therapeutic electrical stimulation of the hypoglossal nerve in obstructive sleep apnea. Arch Otolaryngol Head Neck Surg. Oct. 2001; 127(10):1216-23.

Schwartz AR, Thut DC, Russ B, Seelagy M, Yuan X, Brower RG, Permutt S, Wise RA, Smith PL. Effect of electrical stimulation of the hypoglossal nerve on airflow mechanics in the isolated upper airway. Am Rev Respir Dis. May 1993; 147(5):1144-50.

B. Tucker Woodson, MD, Kingman P. Strohl, MD, Ryan J. Soose, Md, M. Boyd Gillespie, MD, Joachim T. Maurer, MD, Nico de Vries, MD, Tapan A. Padhya, Md, M. Safwan Badr, MD, Ho-sheng Lin, MD, Olivier M. Vanderveken, Md, Phd, Sam Mickelson, MD, and Patrick J. Strollo, Jr. MD. Upper Airway Stimulation for Obstructive Sleep Apnea: 5-Year Outcomes. Otolaryngology—Head and Neck Surgery, Mar. 2018. https://doi.org/10.1177/0194599818762383.

Strollo PJ Jr, Soose RJ, Maurer JT, de Vries N, Cornelius J, Froymovich O, Hanson RD, Padhya TA, Steward DL, Gillespie MB, Woodson BT, Van de Heyning PH, Goetting MG, Vanderveken OM, Feldman N, Knaack L, Strohl KP. Upper-airway stimulation for obstructive sleep apnea. N. Engl J Med. Jan. 9, 2014; 370(2):139-49. doi: 10.1056/NEJMoa1308659.

Heiser C, Hofauer B, Lozier L, Woodson BT, Stark T. Nerve monitoring-guided selective hypoglossal nerve stimulation in obstructive sleep apnea patients. Laryngoscope. Dec. 2016; 126(12):2852-2858. doi: 10.1002/lary.26026. Epub Jun. 27, 2016.

Bassiri Gharb B., Tadisina K.K., Rampazzo A., Hashem A.M., Elbey H., Kwiecien G.J., Doumit G., Drake R.L., Papay F. 2015. Microsurgical Anatomy of the Terminal Hypoglossal Nerve Relevant for Neurostimulation in Obstructive Sleep Apnea, Neuromodulation 2015; E-pub ahead of print. DOI: 10.1111/ner.12347.

Penultimate Official Action/Notice of Reasons for Refusal issued for Japanese Patent Application No. 2022-513142 dated Sep. 22, 2023 (9 pages).

PMDA, Machine equipment 50 Retraction or opening instrument management medical devices single use retractor 13373002 elastic stay, medical devices attached documents, Japan, PMDA, PMDA, Nov. 30, 2017.

Australian Examination Report issued for Australian Patent Application No. 2020335220 dated Feb. 2, 2023 (3 pages).

* cited by examiner

METHOD AND PROCESS FOR PLACEMENT AND FIXATION OF A SURGICAL IMPLANT

This application is a U.S. national stage entry application under 35 U.S.C. § 371 from PCT International Application No. PCT/EP2020/073878, filed on Aug. 26, 2020, which claims benefit of Israeli Patent Application No. 268936, filed on Aug. 26, 2019; the contents of each application is incorporated herein by reference in its entirety.

FIELD OF THE DISCLOSED SUBJECT MATTER

The disclosed subject matter relates to a method and process for placement and fixation of a surgical implant for treatment of sleeping disorders, and in particular sleep apnea.

BACKGROUND OF THE DISCLOSED SUBJECT MATTER

Obstructive sleep apnea is a common and heterogenous condition characterized by repeated partial or complete obstructions of the pharyngeal airway during sleep. In the majority of patients, there is an anatomical predisposition to the disorder. Compounding this may be abnormalities in ventilatory control (such as high loop gain), and an elevated arousal threshold during sleep. The pharyngeal muscles respond to inputs from mechanoreceptors in the airway, as well as changes in oxygen and CO2 levels in the blood. The genioglossus is the major dilator of the pharyngeal airway. Failure of the upper airway dilator muscles to respond appropriately to airflow limitation and or changes in CO2 and O2 levels may lead to obstructive OSA.

Hypoglossal nerve stimulation as a means to dilate the pharyngeal airway was first described by Schwartz et al in a feline model in 1993.

Since then, a few devices (Apnex, Inspire Medical, Imthera) have been developed to stimulate the hypoglossal nerve unilaterally in patients with OSA. The Inspire Medical device has been in use now for over 5 years, and is approved for use in both Europe and North America. The results of the pivotal study of the Inspire hypoglossal nerve stimulator were published in 2014. Whilst the efficacy of this technique has been proven, potential difficulties arise due to MRI compatibility issues, long wires, leads that need to be tunnelled from the chest to the submandibular area, and an embedded battery and processor implanted subcutaneously in the infraclavicular subcutaneous tissues.

REFERENCES

Neelapu B C, Kharband O P, Sardana H K et al, Craniofacial and upper airway morphology in adult obstructive sleep apnea patients: A systematic review and metaanalysis of cephalometric studies. Sleep Med Rev. 2017 February; 31:79-90. doi: 10.1016/j.smrv.2016.01.007. Epub 2016 Jan. 30

Eckert D J, White D P, Jordan A S, Malhotra A, Wellman A Am J Respir Crit Care Med. 2013 Oct. 15; 188(8):996-1004. doi: 10.1164/rccm.201303-04480C Schwartz A R1, Bennett M L, Smith P L, De Backer W, Hedner J, Boudewyns A, Van de Heyning P, Ejnell H, Hochban W, Knaack L, Podszus T, Penzel T, Peter J H, Goding G S, Erickson D J, Testerman R, Ottenhoff F, Eisele D W. Therapeutic electrical stimulation of the hypoglossal nerve in obstructive sleep apnea. Arch Otolaryngol Head Neck Surg. 2001 October; 127(10):1216-23.

Schwartz A R, Thut D C, Russ B, Seelagy M, Yuan X, Brower R G, Permutt S, Wise R A, Smith P L. Effect of electrical stimulation of the hypoglossal nerve on airflow mechanics in the isolated upper airway. Am Rev Respir Dis. 1993 May; 147(5):1144-50.

B. Tucker Woodson, MD, Kingman P. Strohl, MD, Ryan J. Soose, MD, M. Boyd Gillespie, MD, Joachim T. Maurer, MD, Nico de Vries, MD, Tapan A. Padhya, MD, M. Safwan Badr, MD, Ho-sheng Lin, MD, Olivier M. Vanderveken, MD, PhD, Sam Mickelson, MD, and Patrick J. Strollo, Jr, MD. Upper Airway Stimulation for Obstructive Sleep Apnea: 5-Year Outcomes. Otolaryngology—Head and Neck Surgery, March 2018. https://doi.org/10.1177/0194599818762383

Strollo P J Jr, Soose R J, Maurer J T, de Vries N, Cornelius J, Froymovich O, Hanson R D, Padhya T A, Steward D L, Gillespie M B, Woodson B T, Van de Heyning P H, Goetting M G, Vanderveken O M, Feldman N, Knaack L, Strohl K P. Upper-airway stimulation for obstructive sleep apnea. N Engl J Med. 2014 Jan. 9; 370(2):139-49. doi: 10.1056/NEJMoa1308659.

Heiser C, Hofauer B, Lozier L, Woodson B T, Stark T. Nerve monitoring-guided selective hypoglossal nerve stimulation in obstructive sleep apnea patients. Laryngoscope. 2016 December; 126(12):2852-2858. doi: 10.1002/lary.26026. Epub 2016 Jun. 27

Bassiri Gharb B., Tadisina K. K., Rampazzo A., Hashem A. M., Elbey H., Kwiecien G. J., Doumit G., Drake R. L., Papay F. 2015. Microsurgical Anatomy of the Terminal Hypo-glossal Nerve Relevant for Neurostimulation in Obstructive Sleep Apnea.

Neuromodulation 2015; E-pub ahead of print. DOI: 10.1111/ner.12347

A device disclosed in PCT/EP2018/054913 as well as other numerous applications to the applicant, including U.S. Pat. No. 9,415,216, WO2013/046048, U.S. Pat. No. 8,577,466, and incorporated herein by reference, describes hypoglossal nerve stimulators and associated system that have been designed to circumvent some of these issues. By stimulating bilaterally and simultaneously the hypoglossal nerves, the airway opening is potentially more effective than that achieved with unilateral nerve stimulation. Also, there is no need to tunnel wires from the neck down into the chest, and no need for an implanted battery or processor, nor of dissection in the chest.

SUMMARY OF THE DISCLOSED SUBJECT MATTER

In one aspect, a method of treating obstructive sleep apnea comprises:
  providing an implant comprising:
    a substantially planar central body portion having a top side and a bottom side;
    at least two adjustable wing portions; and
    at least two connecting members, each one of the at least two connecting members extending from opposite sides of the central body portion, the each one of the at least two connecting members being configured for flexibly connecting each one of the at least two wing portions at opposite sides to said central body portion;
  forming a surgical opening to expose a genioglossus muscle;

exposing a branch of hypoglossal nerve for stimulation by the implant at least on one side of the genioglossus;

forming at least one pocket superior to the nerve on at least one side of the genioglossus; such that the pocket dimensions are configured to fit the at least one of the at least two wing portions of the device;

inserting an implant device through the surgical opening such that the central body extends over the genioglossus and each one of the wing portions is received in the respective at least one pocket; and securing the implant device to the muscle.

In one embodiment at least one of the at least two adjustable wing portions comprises at least one pair of electrodes. In accordance with this example the electrodes are coupled either mechanically or electrically to an antenna configured to receive a signal and wherein the electrodes being configured to receive an electric current in response to the signal received by the antenna, such that at least one of pair of electrodes is configured to emit an electrical field. In one embodiment, the at least one pair of electrodes extends within the at least one pocket such that when the electrical field is emitted, the hypoglossal nerve is stimulated.

The method may include using a fastening element for securing the implant to the muscle. Such a fastening element may be a suture, an adhesive, or any other type of fastening element including mechanical, chemical or adhesive. In one example, a parachuting technique is used to secure at least the adjustable wing portions. In this embodiment, the suture is used to mark the location of the one or more suturing points and then may be used to secure the wing portions at the pre marked location. In another embodiment, a biodegradable fastening element may be used.

DESCRIPTION OF THE DISCLOSED SUBJECT MATTER

An Implantable Device and System

Figure 1:
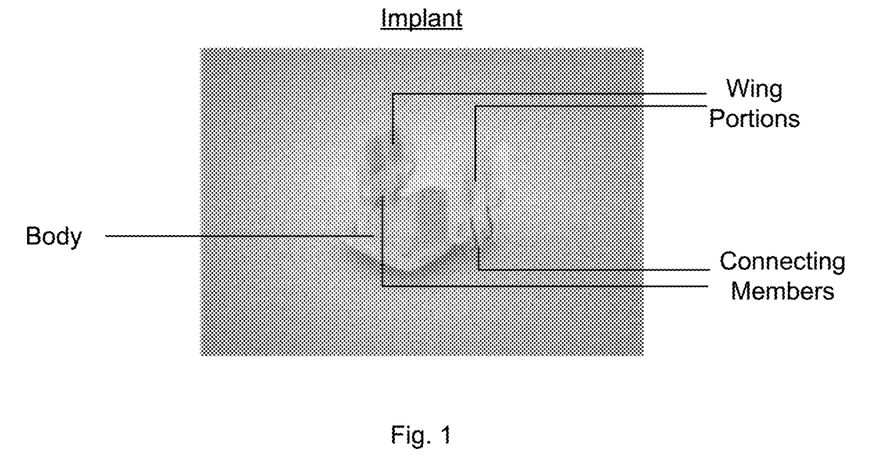
FIG. 1 is an illustration of the implantable device in accordance with an embodiment of the disclosed subject matter.

An example of an implantable stimulator (IS) consists of two sets of paired stimulating electrodes (one on each side of the device—see FIG. 1) and a receiving antenna in the center encased in a silicon envelope to protect the antenna and circuitry. The two sets of electrodes are located on two flexible legs to not only accommodate movement of the genioglossus muscles and hyoid bone, but also to allow for variable neural anatomy. The implant in accordance with the disclosed subject matter comprises:

a substantially planar central body portion having a top side and a bottom side;

at least two adjustable wing portions;

at least two connecting members, each one of the at least two connecting members extending from opposite sides of the central body portion, the each one of the at least two connecting members being configured for flexibly connecting each one of the at least two wing portions at opposite sides to said central body portion.

The IS structure allows positioning over both genioglossus muscles with the stimulating paddle electrodes facing the medial branches of the hypoglossal nerve on each muscle. The flexibility of the wing portions and the connecting members, allows adjustment of the implant over the muscle and further adjustment of each one of the wing portions separately to adapt to the respective anatomy of the muscle and the nerve. The IS is provided sterile. The IS is a passive device as it does not contain a battery in accordance with this example.

Figure 2:
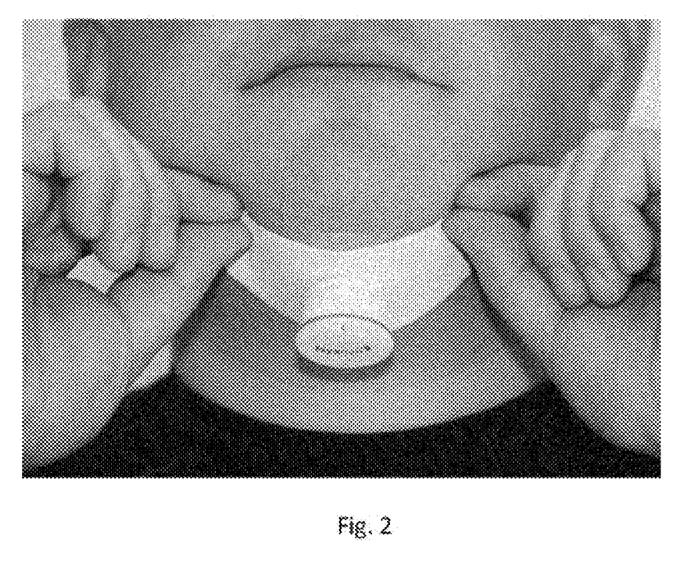
FIG. 2 illustrates placement of the AC-DP over the chin, in accordance with an example of the disclosed subject matter.
Figure 11:
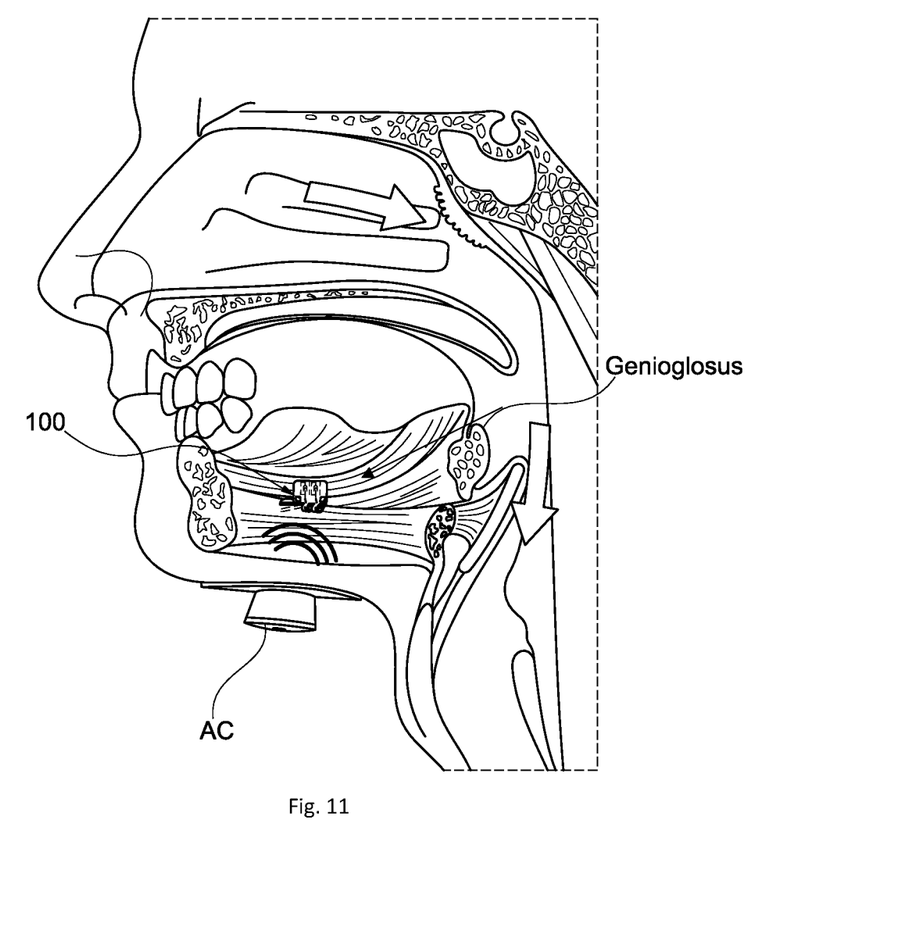
FIG. 11 illustrates the surgical implant in accordance with the disclosed subject matter, e.g. of FIG. 1, positioned over the genioglossus muscle, with the DP and AC provided externally.

In use, and post-surgical procedure, before going to sleep the patient connects an activation chip (AC) to a disposable patch (DP) (both by Nyxoah SA, BE) and then places the DP and AC under the chin (See FIGS. 2 and 11). Examples of Activation chip and the Disposable patch are disclosed in other applications of the applicant, e.g. U.S. Pat. No. 8,577, 468, US2014-0052219 and others, incorporated herein by reference.

A DP is a single-use biocompatible adhesive device; The AC allows the activation of the IS by transferring energy wirelessly. Each morning, the patient removes the AC from the DP and discards the DP.

The storage memory of the AC contains the user-specific stimulation parameters programmed by the treating physician.

Patient Setup

Figure 3:
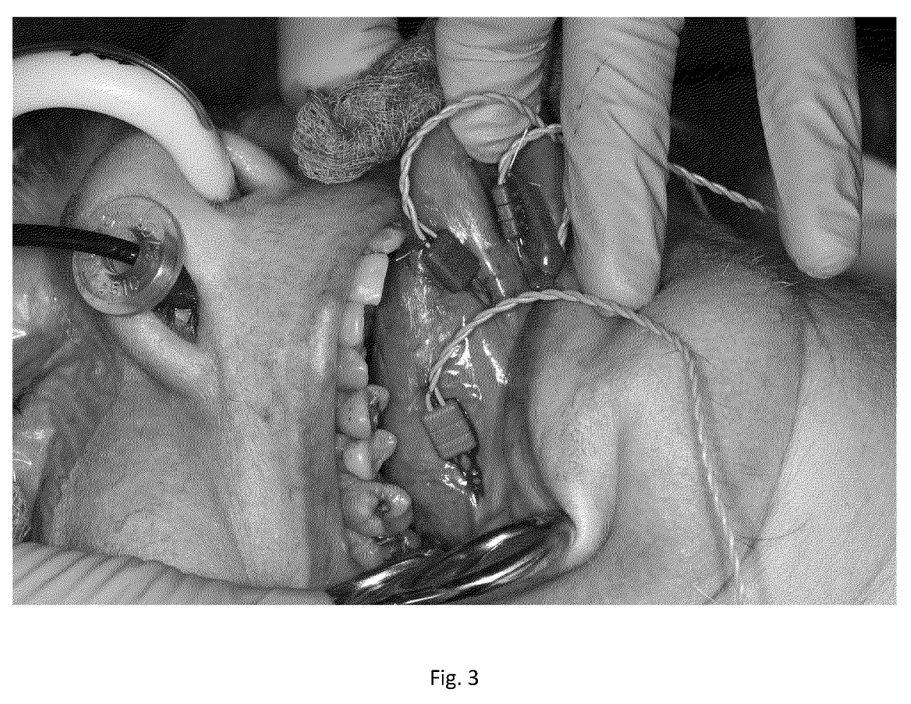
FIG. 3 is an image of the patient set up prior to surgery, in accordance with the disclosed subject matter.

Under general anaesthesia with nasotracheal intubation, the patient is placed in a supine position and the neck extended with a shoulder roll. Four electrodes connected to the nerve integrity monitoring system are inserted into the tongue in order to locate the medial branches of the hypoglossal nerve and or the terminal fibers thereof and to verify proper muscle contraction: one set of electrodes in each genioglossus muscle, and the other one in each styloglossus muscle[i] (see FIG. 3).

The bipolar electrodes are sutured to the tongue mucosa to prevent them moving, with 3/0 vicryl (Ethicon Inc, USA). The electrodes are carefully gathered to one corner of the mouth and secured to the facial skin near the mouth with adhesive tapes. A gauze roll is inserted between the teeth laterally to keep the mouth open so that tongue movement can be observed during stimulation. Finally, a videonasendoscope is inserted and a view of the epiglottis and tongue base achieved. Tape is placed around the scope at the level of the nostril to mark the depth at which the epiglottis is seen. Then, the scope is laid on the operating table next to the patient's head and unplugged from the monitor. This will be covered by the drapes, and the anaesthetist can still access it. Some gauze is laid over the scope near the nose, to stop the sterile drapes from sticking to it. Alternatively, a nasopharyngeal airway may be inserted to facilitate easy insertion of the nasendoscope at any time.

Implantation Technique

Figure 4:
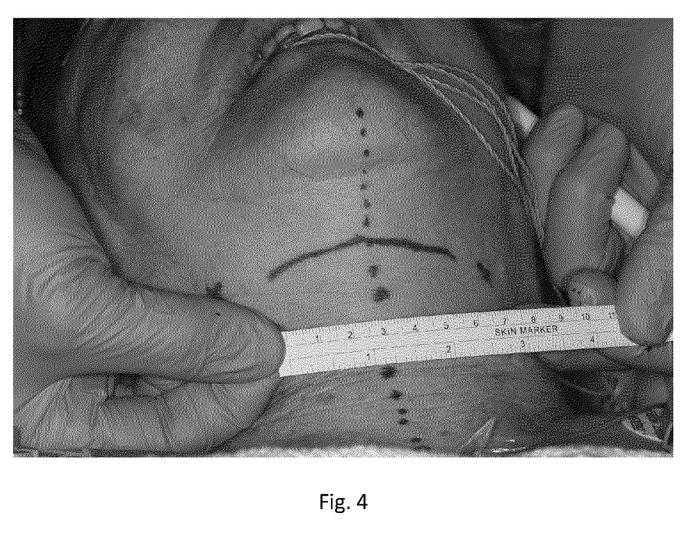
FIG. 4 is an illustration of the patient marking and set up for surgical procedure, prior to surgery.

The midline is marked by a dotted line from the mentum down to the thyroid notch. The hyoid bone is marked with a horizontal line. The midpoint between the hyoid bone and the mentum is marked. A horizontal skin incision is then marked, 4 to 6 cm in length, at the level of the midpoint between the hyoid and the mentum. In addition, a dotted line used for reference is drawn to mark the midline (See FIG. 4).

5 ml of local anaesthetic and adrenaline (1% xylocaine with 1/100000 adrenaline) is injected into the skin along the line of the incision. The skin is sterilised with betadine from the sternal notch to the nose, and as far laterally to at least the greater cornua of the hyoid.

A split sheet drape is placed from approximately the lower border of the thyroid cartilage, with a second sheet placed just below the nostrils, leaving the mouth uncovered. Then, a clear sterile plastic sheet is placed over the mouth/nose/upper drape, leaving the sterile neck exposed.

Figure 5:
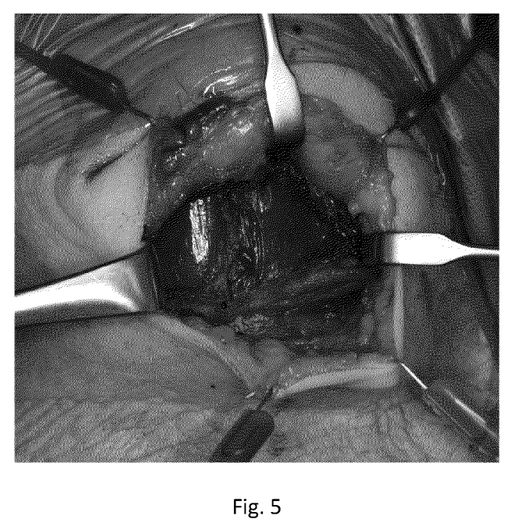
FIG. 5 is an illustration of a surgical step, exposing the GH muscle.

Following 2 g intravenous Cefazolin, the transverse incision is made. Monopolar cautery with a needle or spatula tip is used to deepen the incision through the platysma. Sub-platysmal flaps are raised up to the mentum and down to the thyroid notch. Four Lone-Star elastic stays (Cooper Surgical, Trumbull, CT, USA) or fish hooks are used to retract the skin flaps. Cautery is then used to dissect vertically in the midline through fat down to the mylohyoid muscle. Adherence to the midline is assisted by reference to the vertical skin marking indicating the midline. With the assistant providing countertraction, dissection is continued carefully through the mylohyoid. With loupe magnification, the horizontal fibres of the mylohyoid are easily identified and divided. When the mylohyoid has been divided, the vertical fibres of the geniohyoid muscles (GH) will be immediately apparent (See FIG. 5).

Figure 6:
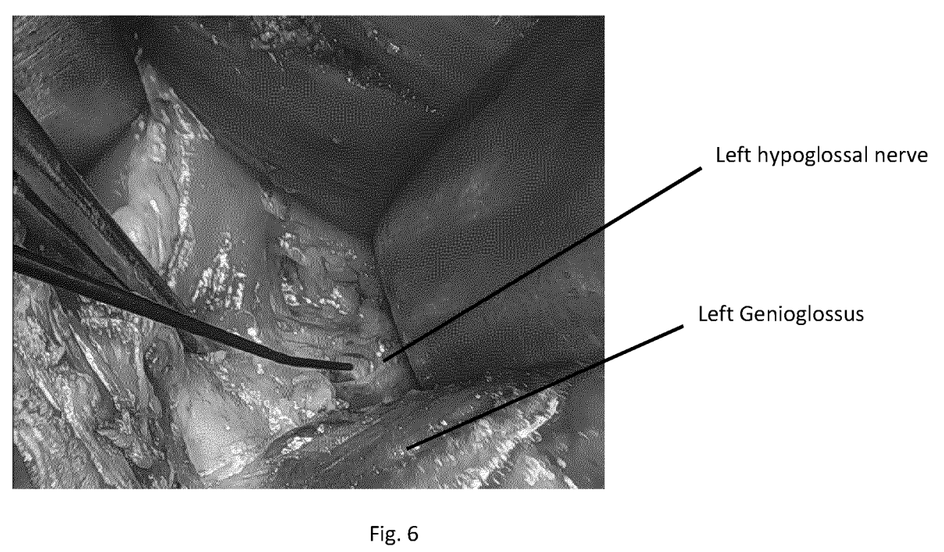
FIG. 6 is an illustration of the surgical opening, with exposed Hypoglossal nerve and the left GG muscle.

The GH muscles are usually tightly apposed in the midline, and therefore determining the midline between the two muscle bellies can sometimes be challenging. Elevating a little of the mylohyoid from the GH muscles, and then searching superiorly to the mandible and inferiorly right down to the hyoid bone can make identifying the plane between the GH muscles easier. The GH muscles are carefully separated using tenotomy scissors and bipolar cautery (or unipolar diathermy to avoid bleeding), from the mandible right down to the hyoid bone. The assistant retracts the muscle bellies and gentle separation of them continues in the midline until the genioglossus muscles (GG) are identified. The fatty midline raphe between the GG muscles is readily identified. At that point, it is important to not dissect between the GG muscles, but to carefully dissect the geniohyoid muscles off them. If the surgeon is standing on the patient's right, it is easier to dissect the left/opposite GH off the GG initially, using tenotomy scissors, Leahy dabs, and bipolar cautery as needed. The assistant uses retractors to elevate the muscle. The lateral border of the GG is then identified, and the fat lateral to it is carefully explored to find the hypoglossal nerve. The nerve passes superomedially to intersect the GG at an angle of approximately 70 degrees (See FIG. 6). The stimulator probe of the NIM may then be used to assist location of the nerve. The stimulus intensity may be set quite high (0.5 to 1 mAmp) until the nerve is more precisely located.

Figure 7:
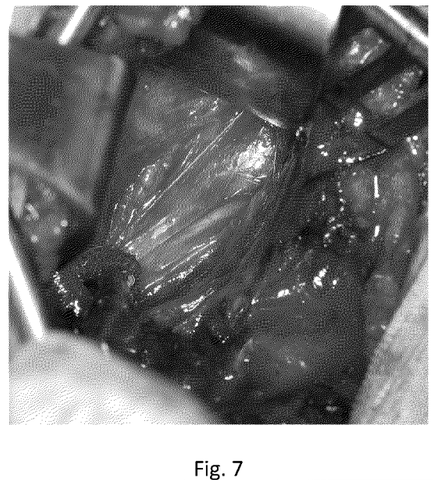
FIGS. 7 and 8 are illustrations of the exposed nerves.

Almost invariably, there is a vein lateral to the nerve (a vena comitans), which precludes a clear view of the superior aspect of the nerve. This may be gently dissected off the nerve, cauterised with bipolar cautery, and then divided. The nerve should be dissected cleanly on its superior aspect, and a deep pocket made superior to the nerve. The pocket needs to be made deep and wide enough to fit the legs of the device in without any external force. Dissection of the nerve as close to the GG as possible will reduce the likelihood of any retrusor branches or the C1 branch being stimulated (see FIG. 7).

If branches are seen, they should be stimulated with the NIM to determine whether or not they are retrusor branches. Occasionally the lingual artery will be seen when dissecting this pocket. Bleeding is usually venous and can be controlled with topical adrenaline on cottonoids, and bipolar cautery.

Figure 8:
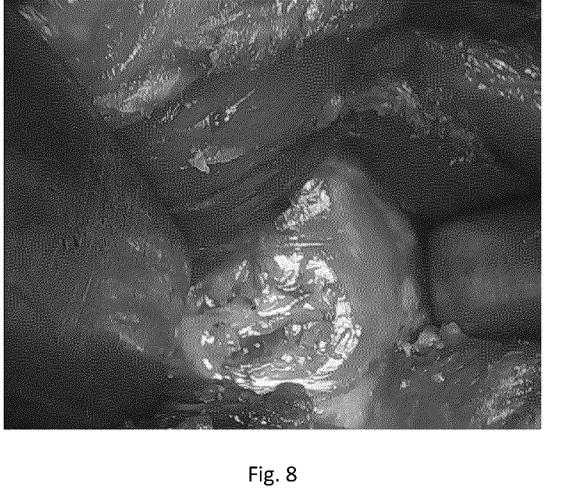

Once the nerve has been exposed on its superior aspect, and the pocket made, the NIM stimulator is used to confirm electrode position. It is important to reduce the stimulus intensity to 0.1 mAmp. This will avoid retrograde stimulation of the hypoglossal nerve which could cause spurious stimulation of the styloglossus electrode. If significant stimulation of the styloglossus still occurs at 0.1 mAmp, then careful dissection is carried out to look for a branch to this muscle (see FIG. 8) which will head superiorly. If found, it should be gently dissected away from the medial continuation of the hypoglossal nerve, and the pocket made medial to the branch.

In accordance with an example of the disclosed subject matter, when positioning the electrodes to induce contraction of the GG, it is advantageous to avoid stimulating any branches of the nerve that might lead to tongue retraction, i.e. retrusors such as styloglossus or hyoglossus. In one example, a respective branch is placed under a direct vision.

As the branch to styloglossus leaves the hypoglossal nerve proximal to that of hyoglossus, in one example NIM electrodes are placed in both hyoglossus and both genioglossus muscles directly during the surgery and connected to a NIM monitor. This step can be performed in addition to placement of the NIM electrodes in the mouth. Such a combination will allow comparing the responses of the two sets.

The process is then repeated for the right nerve, with the surgeon switching sides and standing on the left side of the patient.

Figure 9:
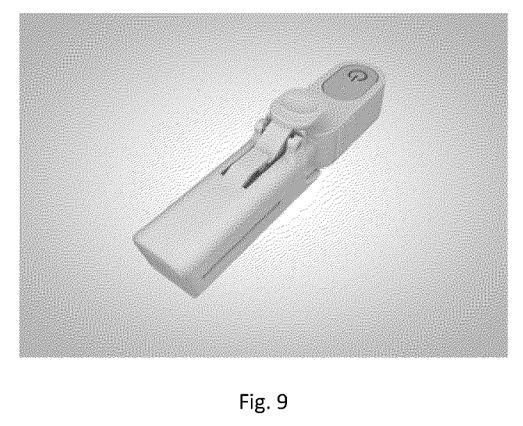
FIG. 9 is an illustration of an external stimulator (ES), in accordance with the disclosed subject matter.

After surveying for and controlling any bleeding, irrigate the pocket with saline to wash away any clot and ensure no active or potential bleeder. Then, the implant is placed into position, and one electrode is inserted into its pocket. It is important to make sure that the nerve passes across both electrodes. If the device leg does not sit comfortably in the pocket, then the pocket should be made a little larger, and the device leg re-inserted. If the position is satisfactory, the External Stimulator (ES) (See FIG. 9) is turned ON and placed perpendicularly over the device antenna so the implant can be activated and the therapy effect tested. Initially the stimulator should be set at its maximum distance using the retractor so the minimum amount of energy is transmitted to the device.

Then the distance should be gradually reduced until there is strong contraction of the tongue. The NIM monitor should display high potentials in the genioglossus electrode with a low reading in the styloglossus electrode. If the styloglossus electrode is showing a similar reading to the GG electrode, the position of the IS can be moved, and this will often lead to a high GG and low SG reading. If it cannot be improved, then the electrode position may need to be adjusted, with further medial dissection of the nerve if possible, and separation of any retrusor branches or the C1 branch if they can be identified. When the readings are satisfactory, and the tongue contraction looks strong, the electrode is fixed in place with 2×3/0 Ethibond sutures (Ethicon Inc, NJ, USA) placed through the dedicated suture holes located on each device leg. Non-toothed forceps only must be used, and the device electrodes should never be in contact with any metal. The IS leg should only be held using non-toothed forceps at the suture holes, or by the fingers. The suture should initially be passed through the device, and then through the soft tissue before tying the knots. This is to prevent inadvertently puncturing the device in a location other than the dedicated suture holes, which could cause damage to the circuitry and lead to malfunction.

The same process is repeated for the other side. Then, the antenna part of the IS is sutured to the genioglossus muscles. Once again, it is important to pass the sutures through the dedicated suture holes in the device first, and then the soft tissue. A small right-angle clamp (Mixter) can be used to support the device on its deep surface which makes it easier to push the suture needle through the suture holes.

The device should then be tested under stimulation with the AC. To do this, the skin edges are temporarily closed with a single suture, and a large sheet of clear sterile plastic is placed over the neck and face to cover the sterile area. The technician then holds a patch (DP) and external stimulator (AC) over the implant, and the responses on the NIM monitor as well as the movement of the tongue, epiglottis and palate observed with the endoscope. If there is severe asymmetry in thresholds or movement, then the electrodes may need to be repositioned. Once the responses are satisfactory, then the plastic sheet is lifted off the sterile field, the temporary skin suture removed to reopen the neck, and the wound irrigated with sterile saline. The depth between the implant receiver and the skin should be measured. If it is more than 4 cm, then some fat may need to be removed. This can be removed either superficial or deep to platysma, or both. The geniohyoid muscles are sutured together with a few interrupted 3/0 vicryl sutures, then the mylohyoid muscle repaired with several 3/0 vicryl sutures. The platysma is closed with a running 3/0 vicryl, and the skin closed with a 4/0 Monocryl (Ethicon Inc, NJ, USA) subcuticular suture. A drain is not necessary and best avoided to prevent the potential for infection, unless there has been significant fat removal. In that case, a small suction drain or Penrose drain may be used. A waterproof dressing is applied. One final check of the implant is performed with the technician holding the AC/DP, and the endoscope manipulated to try to get a view of the airway.

The patient is then extubated and transferred to the recovery room and then the ward.

Postoperative Management

Figure 10:
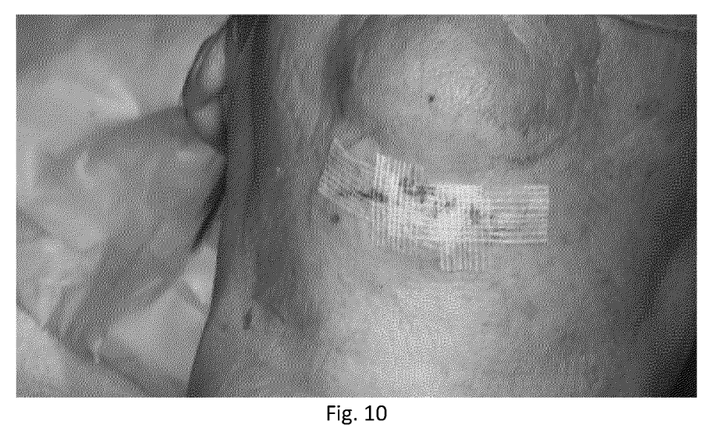
FIG. 10 illustrates post-operative incision area.

Analgesia requirement are minimal, with pain scores usually 2/10. Free oral intake is allowed. The patient is reviewed the next morning and discharged home as long as there are no contraindications. They are instructed to keep the waterproof dressing on for 5 days then remove it, and a review is scheduled for 7 days following surgery (See FIG. 10).

The patient is booked in for a one month appointment to activate the device. Initially a low stimulus setting is programmed to help the patient get used to the sensation of tongue stimulation. Two weeks later, the first titration sleep study is booked at which the stimulus will be titrated.

Example

A 55 year old female with severe OSA (AHI 73, nadir O2 saturation 79%) was intolerant of nasal CPAP. She could only manage 1-2 hours of CPAP use each night, and consequently suffered excessive daytime tiredness. Her general health was otherwise excellent.

Examination revealed a slim lady with mildly recessive upper and lower jaws, and good nasal airways. She had a Friedman grade 2 tongue position, and grade 2 tonsils. Endoscopic examination revealed AP narrowing of the retropalatal airway, and to a lesser degree the retrolingual airway. There was no lingual tonsillar hypertrophy. Jaw thrust improved the airway at all levels.

In 2016, she underwent modified UPPP, transpalatal advancement pharyngoplasty, and radiofrequency tongue channelling.

She made an uneventful recovery, and her 3 month post-operative PSG showed an AHI of 27 (preop 73), and a nadir SaO2 of 92%. However, her supine AHI was unchanged at 77.8. Whilst her Epworth Sleepiness Scale had decreased from 18 to 4, she was still subjectively tired, and turning onto the back resulted in severe apnoea with frequent awakenings.

Once again, she declined to retry CPAP, and declined the offer of a mandibular advancement splint. She was screened for the Nyxoah Hypoglossal Nerve Stimulator and successfully passed the screening.

Her DISE showed AP retrolingual obstruction, with no significant retropalatal obstruction. She was discharged the morning after surgery, and had an uneventful recovery.

Her baseline screening PSG and 2 month titration PSG figures are below:

|  | Baseline | 2 Month Titration |
|---|---|---|
| AHI/hr | 25.3 | 3.6 |
| Obstructive apnoea/hr | 7.3 | 0 |
| Hypopnoea/hr | 15.4 | 3.5 |
| ODI/hr | 23.7 | 1.9 |

Figure 12:
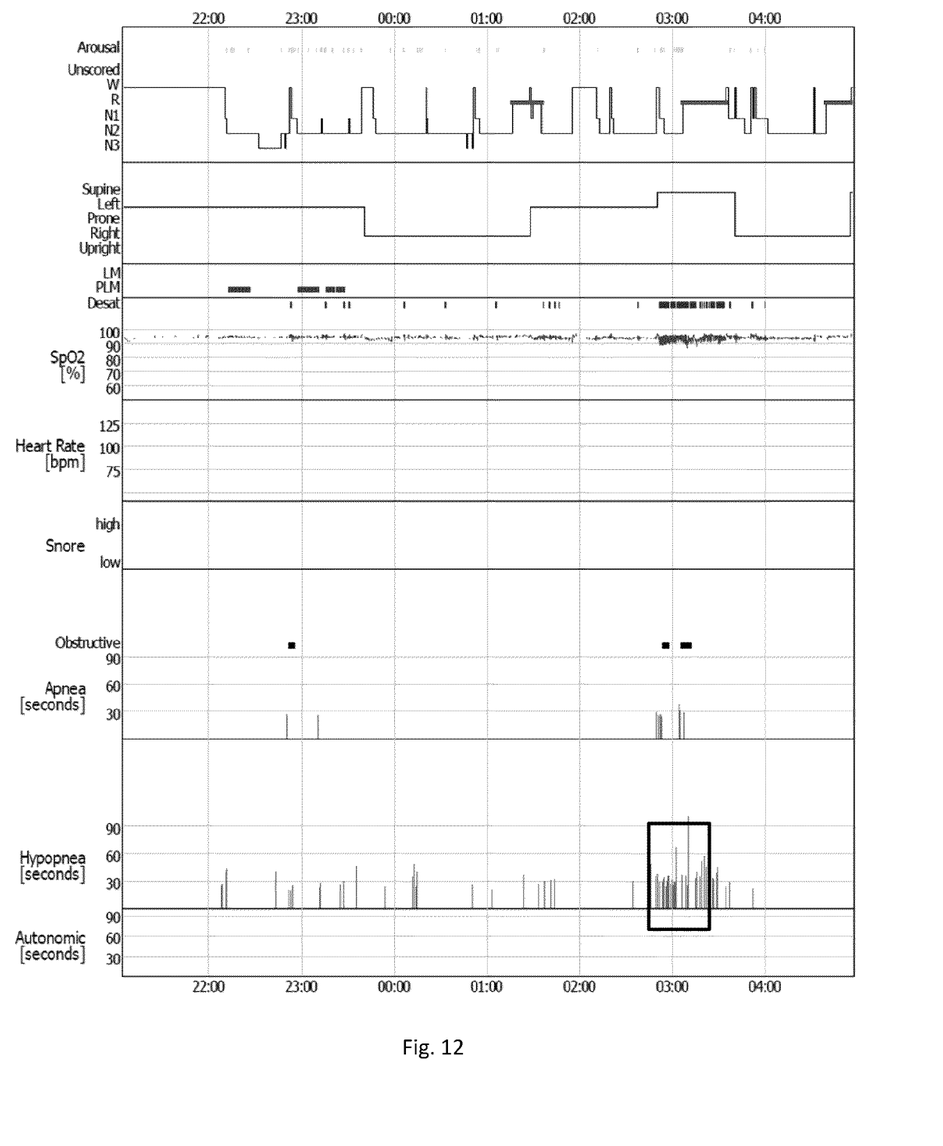
FIG. 12 illustrates a screenshot of PSG result.

In the 3 month titration PSG, the device was turned off at 02:48 and turned back on at 03:19 to demonstrate the effectiveness in controlling the OSA. This is highlighted in the box on the PSG in FIG. 12.

Although various embodiments disclosed herein relate to use in humans, it is contemplated that the present invention may be used in all mammals, and in all animals having air passages.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to.

While the foregoing is directed to embodiments of the present disclosed subject matter and examples, other and further embodiments of the disclosed subject matter may be devised without departing from the basic scope thereof.

The invention claimed is:

1. A method of treating obstructive sleep apnea, comprising:
   providing an implant device comprising:
   a substantially planar central body portion having a top side and a bottom side;
   at least two adjustable wing portions; and
   at least two connecting members, each one of the at least two connecting members extending from opposite sides of the central body portion, the each one of the at least two connecting members being configured for flexibly connecting each one of the at least two wing portions at opposite sides to said central body portion;

forming a surgical opening to expose a genioglossus muscle;

exposing a branch of a hypoglossal nerve for stimulation by the implant at least on one side of the genioglossus muscle of a patient;

forming at least one pocket on at least one side of the genioglossus muscle such that dimensions of the at least one pocket are configured to fit the at least one of the at least two wing portions of the implant device;

inserting the implant device through the surgical opening such that the central body extends over the genioglossus muscle and each one of the wing portions is received in the respective at least one pocket;

positioning the implant device based on a determination of a relative amount of stimulation potential for both a styloglossus nerve and the hypoglossal nerve by the implant device; and securing the implant device to the muscle.

2. The method of claim 1, further comprising determining the relative amount of stimulation potential for both a styloglossus nerve and the hypoglossal nerve by the implant device.

3. The method of claim 2, wherein determining the relative amount of stimulation potential comprises determining that a stimulation potential for the hypoglossal nerve exceeds a stimulation potential for the styloglossus nerve.

4. The method of claim 1, further comprising inserting a gauze to keep a mouth of the patient open.

5. The method of claim 1, further comprising dissecting at least one geniohyoid muscle off of the genioglossus muscle.

6. The method of claim 1, further comprising dissecting a vein off of the hypoglossal nerve.

7. The method of claim 1, further comprising holding each of the at least two adjustable wing portions using at least one of non-toothed forceps or fingers.

8. The method of claim 1, further comprising elevating the genioglossus muscle.

* * * * *